United States Patent
Chun et al.

(10) Patent No.: US 6,423,252 B1
(45) Date of Patent: Jul. 23, 2002

(54) METHODS OF MAKING MICROPATTERNED FOAMS

(75) Inventors: Iksoo Chun, Flemington; Yufu Li; Mora C. Melican, both of Bridgewater, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/602,926

(22) Filed: Jun. 23, 2000

(51) Int. Cl.[7] .............................................. B29C 44/02
(52) U.S. Cl. ............................. 264/28; 264/41; 264/101
(58) Field of Search ........................... 264/41, 28, 101, 264/102

(56) References Cited

U.S. PATENT DOCUMENTS

| | | | | |
|---|---|---|---|---|
| 4,186,448 A | * | 2/1980 | Brekke ........................ | 128/898 |
| 4,242,291 A | * | 12/1980 | Hughes et al. ............. | 264/1.21 |
| 5,116,552 A | * | 5/1992 | Morita et al. ................. | 264/28 |
| 5,133,755 A | * | 7/1992 | Brekke ........................ | 623/16 |
| 5,514,378 A | * | 5/1996 | Mikos et al. ................ | 424/425 |
| 5,522,895 A | * | 6/1996 | Mikos ......................... | 623/16 |
| 5,607,474 A | * | 3/1997 | Athanasiou et al. ......... | 623/11 |
| 5,677,355 A | * | 10/1997 | Shalaby et al. .............. | 521/61 |
| 5,686,091 A | * | 11/1997 | Leong et al. ............... | 424/426 |
| 5,711,960 A | * | 1/1998 | Shikinami ................... | 424/426 |
| 5,716,413 A | * | 2/1998 | Walter et al. ................. | 623/16 |
| 5,755,792 A | * | 5/1998 | Brekke ........................ | 623/16 |
| 5,769,899 A | * | 6/1998 | Schwartz et al. ............. | 623/18 |
| 5,770,193 A | * | 6/1998 | Vacanti et al. ............ | 424/93.7 |
| 5,847,012 A | * | 12/1998 | Shalaby et al. .............. | 521/61 |
| 5,898,040 A | | 4/1999 | Shalaby et al. | |
| 5,969,020 A | * | 10/1999 | Shalaby et al. ............ | 524/167 |

FOREIGN PATENT DOCUMENTS

| WO | WO 95/05083 A1 | 2/1995 |
|---|---|---|
| WO | WO 96/40002 A1 | 12/1996 |
| WO | WO 99/47922 A2 | 9/1999 |

OTHER PUBLICATIONS

E. T. Den Braber, et al., *Orientation of ECM Protein Deposition, Fibroblast, Cytoskeleton, and Attachment Complex Components on Silicon Microgrooved Surfaces*, J. Biomed.Mat.Res., 1998, 291, vol. 40, 291.

K. Kieswetter, et al., *Surface Roughness Modulates The Local Production of Growth Factors and Cytokines by Osteoblast–like MG–63 Cells*, J. Biomed.Mat. Res., 1996, 55–63, vol. 32.

J. Y. Martin, et al., *Effect of Titanium Surface Roughness on Proliferation, Differentiation, and Protein Synthesis of Human Osteoblast–like Cells (MG63)*, J. Biomed. Mat. Res., 1995, 389–401, vol. 29.

D. Buser, et al., *Influence of Surface Characteristics on Bone Integration of Titanium Implants. A Histomorphometric Study in Miniature Pigs*, 1991, 889–902, vol. 25.

Kevin A. Thomas, et al., *An Evaluation of Variables Influencing Implant Fixation by Direct Bone Apposition*, 1985, 875–901, vol. 19.

(List continued on next page.)

*Primary Examiner*—Allan R. Kuhns

(57) ABSTRACT

The present invention is directed to a method of making a foam, the method including contacting a polymer solution with a surface of a mold, the solution containing dissolved therein a biocompatible polymer, the mold containing disposed on at least one surface thereof a three-dimensional negative configuration of a predetermined micropattern to be disposed on and integral with at least one surface of the foam, lyophilizing the solution while in contact with the surface of the mold and removing the lyophilized micropatterned foam from the mold.

19 Claims, 5 Drawing Sheets

OTHER PUBLICATIONS

J. L. Ricci, et al., *Morphological Characteristics of Tendon Cells Cultured on Synthetic Fibers*, 1984, 1073–1087, vol. 18.

Kurt T. Bowers, DDS., et al., *Optimization of Surface Micromorphology for Enhanced Osteoblast Responses in Vitro*, 302–310, vol. 7. (1992).

Lars Carlsson, M.D., et al., *Removal Torques for Polished and Rough Titanium Implants*, 1988, 21–24, vol. 3.

Tessa Hadlock, M.D., et al., *A Polymer Foam Conduit Seeded with Schwann Cells Promotes Guided Peripheral Nerve Regeneration*, 2000, 119–127, vol. 6.

Z. Schwartz, et al., *Underlying Mechanisms at The Bone–Biomaterial Interface*, 1994, 340–347, vol. 56.

H. J. Wilke, et al., *The Influence of Various Titanium Surfaces on the Interface Shear Strength Between Implants and Bone*, 1990, 309–314, vol. 9.

\* cited by examiner

METHODS OF MAKING MICROPATTERNED FOAMS

FIELD OF THE INVENTION

The present invention relates to methods of making biocompatible foams having a micropatterned surface disposed on and integral with at least one surface of the foam.

BACKGROUND OF THE INVENTION

Open-cell, porous, biocompatible foams have been recognized to have significant potential for use in the repair and regeneration of tissue. Early efforts in tissue repair focused on the use of amorphous biocompatible foam as porous plugs to fill voids in bone. Brekke, et al. (U.S. Pat. No. 4,186,448) described the use of porous mesh plugs composed of polyhydroxy acid polymers such as polylactide for healing bone voids. Several attempts have been made in the recent past to make tissue engineering (TE) scaffolds using different methods. For example, U.S. Pat. No. 5,522,895 (Mikos) and 5,514,378 (Mikos, et al.) using leachables; U.S. Pat. No. 5,755,792 (Brekke) and 5,133,755 (Brekke) using vacuum foaming techniques; U.S. Pat. No. 5,716,413 (Walter, et al.) and 5,607,474 (Athanasiou, et al.) using precipitated polymer gel masses; U.S. Pat. No. 5,686,091 (Leong, et al.) and 5,677,355 (Shalaby, et al.) using polymer melts with fugitive compounds that sublimate at temperatures greater than room temperature; and U.S. Pat. No. 5,770,193 (Vacanti, et al.), 5,769,899 (Schwartz, et al.) and 5,711,960 (Shikinami) using textile-based fibrous scaffolds. Hinsch et al. (EPA 274,898) describes a porous, open-cell foam of polyhydroxy acids with pore sizes from about 10 to about 200 µm for the in-growth of blood vessels and cells. The foam described by Hinsch could also be reinforced with fibers, yarns, braids, knitted fabrics, scrims and the like.

The above techniques have limitations in producing porous scaffolds with controlled surface textures. The scaffolds are smooth-walled and lack the surface features that encourage the attachment of cells, their proliferation, and their differentiation into phenotypes appropriate for the specific tissue type.

Surface features are known to influence cell adhesion, migration, proliferation, and differentiation. The adhesion and migration of osteoblasts along surface features on implants has been studied extensively by many groups, including Jack Ricci et al. (See Morphological Characteristics of Tendon Cells Cultured On Synthetic Fibers, J. Biomed. Mater. Res., J. Ricci et al., Vol. 18, pages 1073–87, 1984.) The influence of surface topography on the proliferation and differentiation of osteoblast-like MG-63 cells has been described in Surface Roughness Modulates the Local Production of Growth Factors and Cytokines by Osteoblast-like MG-63 Cells, J. Biomed. Mater. Res., Kieswetter et al., Vol. 32, pages 55–63, 1996 and Effect of Titanium Surface Roughness on Proliferation, Differentiation, and Protein Synthesis of Human Osteoblast-like Cells (MG63), J. Biomed. Mater. Res., Martin et al., Vol. 29, pages 389–401, 1995.

The ideal implant surface is one that promotes tissue ingrowth and healing. In the case of bone, four surface properties of implants play a role in the attraction of primitive mesenchymal stem cells, and their differentiation into osteoblasts at the bone implant interface during the healing process. The four surface properties are composition, surface energy, topography and roughness. This is described in further in Underlying Mechanisms at the Bone-biomaterial Interface, J. Cell. Biochem., Z. Schwartz et al., Vol. 56, pages 340–7 1994. Another study described in An Evaluation of Variables Influencing Implant Fixation by Direct Bone Apposition, J. Biomed. Mater. Res., K. Thomas et al., Vol. 19, pages 875–901, 1985, has shown that texture, defined as a combination of roughness and topography, plays a greater role in cell response than implant material.

Textured implant surfaces have been shown to produce better bone fixation than smooth surfaced implants, see Removal Torques For Polished and Rough Titanium Implants, Int. J. Maxillofac. Impl., L. Carlsson et al., Vol. 3, pages 21–24, 1988 and The Influence of Various Titanium Surfaces on the Interface Shear Strength Between Implants and Bone, Clinical Implant Materials: Advances in Biomaterials, H.-J. Wilke et al., Vol. 9, pages 309–314, 1990. Surface patterning has been shown to have a great effect on cell behavior, both in tissue culture experiments (See Optimization of Surface Micromorphology for Enhanced Osteoblast Responses In Vitro, Int. J. Oral Maxillofac. Impl., K. Bowers et al., Vol. 7, pages 302–310, 1992) and in vivo (See Influence of Surface Characteristics on Bone Integration of Titanium Implants: A Histomorphometric Study in Miniature Pigs, J. Biomed. Mater. Res., D. Buser et al., Vol. 25, pages 889–902, 1991.) In addition, the effect of implant surface texture on the type of extracellular matrix (ECM) produced has been described in Orientation of ECM Protein Deposition, Fibroblast Cytoskeleton, and Attachment Complex Components on Silicon Microgrooved Surfaces, J. Biomed. Mater. Res., E. Den Braber et al., Vol. 40, page 291, 1998.

Several multi-step processes for making textured surfaces on polymeric foams are known. Shalaby and Roweton (U.S. Pat. Nos. 5,969,020, 5,899,804, 5,847,012, 5,677,355 and WO 9505083) describe a process for creating patterns of pores on foam surfaces via the extraction of a fugitive material to foam the polymer. Another approach to make foams with patterned surfaces is proposed by Griffith et al. (WO9947922).

The limitation of the above-described techniques for forming foams with patterned surfaces is that they require multiple processing steps. As the number of processing steps is increased, the possibility of rejection of the final product is increased, as well as the cost of the resulting product.

Yet another approach to making foams with patterned surfaces is described by Vacanti et al. (WO9640002). Here, several solid free-form fabrication (SFF) processes are described. Examples of SFF methods include stereo lithography (SLA), selective laser sintering (SLS), ballistic particle manufacturing (BPM), fusion deposition modeling (FDM), and three-dimensional printing (3DP). An additional approach to create porous polymeric structures with channels is described in A Polymer Foam Conduit Seeded with Schwann Cells Promotes Guided Peripheral Nerve Regeneration, Tissue Engineering, Hadlock et al., Vol. 6, pages 119–127, 2000.

All processes noted above either require an additional step to produce the textured surface via etching, micromachining, punching, leaching, round razor or laser drilling, or other similar process, or are very complex and require specialized expensive equipment. Further, the resulting patterned surfaces are not completely integrated into the structures and may be subjected to differences in degradation and tissue response under in vivo conditions.

The present invention provides a simple, one-step process for making biocompatible foams containing a micropattern disposed on and integral with at least one surface of the foam. The structure of the micropattern provides organization at the microstructure level and a template that facilitates cellular invasion, proliferation and differentiation, thus ultimately resulting in regeneration of functional tissue.

Summary of Invention

The present invention is directed to a method of making a foam, the method comprising contacting a polymer solution with a surface of a mold, the solution comprising dissolved therein a biocompatible polymer, the mold comprising disposed on at least one surface thereof a three-dimensional negative configuration of a predetermined micropattern to be disposed on and integral with at least one surface of the foam, lyophilizing the solution while in contact with the micropatterned surface of the mold, thereby providing a lyophilized, micropatterned foam, and removing the lyophilized, micropatterned foam from the mold. Foams prepared according to the invention comprise a predetermined and designed micropattern on at least one surface, which pattern is effective to facilitate tissue repair, ingrowth or regeneration, or is effective to provide delivery of a protein or a therapeutic agent.

The tissue response to scaffolds with such designed surfaces can be tailored depending on the desired response. Changing the surface micropattern will alter the bioabsorption profile, and will provide a different microenvironment for cell adhesion and migration, both of which are advantageous in a variety of medical applications.

Preferred micropatterned structures are particularly useful for the regeneration of tissue between two or more different types of tissues. For a multi-cellular system in the simplest case, a first cell type could be present on one side of the foam scaffold with a specific, predetermined surface micropattern designed to facilitate growth of the cell, while a second cell type could be present on the other side of the foam scaffold with a different predetermined micro-pattern designed to facilitate growth of the second cell type. Examples of such regeneration include, without limitation, (a) vascular tissue: with smooth muscle on the outside and endothelial cells on the inside to regenerate vascular structures; and (b) osteochondral tissue: by implanting with a surface micropattern that attracts chondrocytes on one surface of the foam and a different micro-structure that attracts osteoblasts or pre-osteoblasts on the opposing surface.

DETAILED DESCRIPTION OF THE INVENTION

Figure 1:
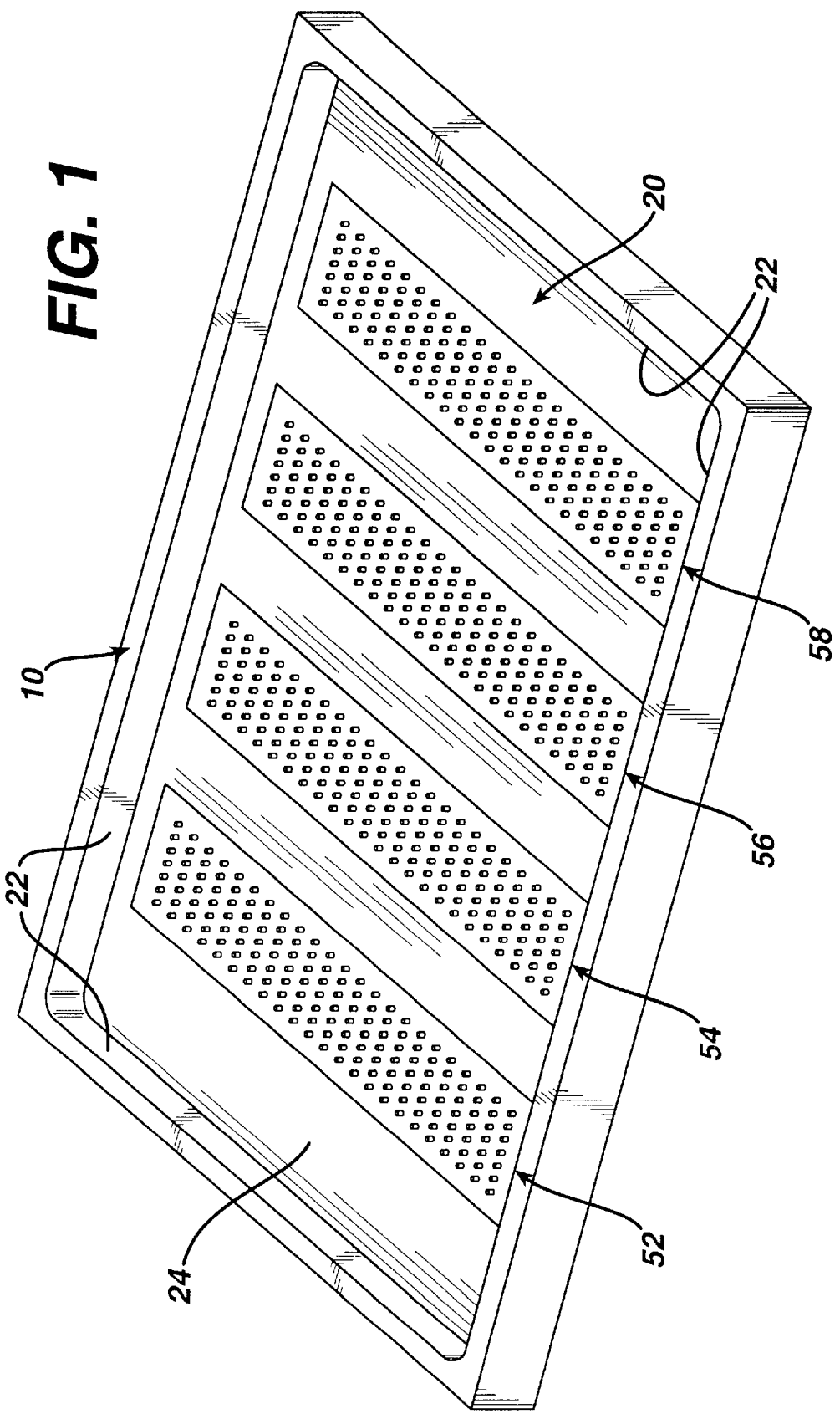
FIG. 1 is a perspective view of a micropatterned mold used in the present invention.

It is preferred that foams used in tissue engineering (i.e. tissue repair, ingrowth or regeneration) have a micropattern disposed on and integral with a surface of the foam that provides organization at the microstructural level, that provides a template that facilitates cellular organization and regeneration of tissue, that has the anatomical, biomechanical, and biochemical features of normal tissues. These micropatterned foams can be used to repair, ingrow or regenerate tissue (including organs) in animals, such as domestic animals, primates and humans. The present invention provides methods for making porous, biocompatible, bioabsorbable polymeric foam that contain such a micropattern disposed on and integral with at least one surface of the foam. The micropattern(s) to be disposed on and integral with the surface(s) of such foams can be designed to suit a specific, predetermined application by lyophilizing the foam in a mold that has a three-dimensional negative configuration of the predetermined and designed micropattern disposed on at least one of the walls, floor, or lid of the mold that is to be contacted with the polymer solution. Absorbable polymeric foam scaffolds having such micropatterned surface features have distinct advantages over scaffolds having smooth surfaces.

The micropatterned surface features of such foams can be controlled to suit predetermined and desired application by selecting the appropriate mold patterns to obtain one or more of the following properties: (1) pores of controlled sizes that provide pathways for cellular ingrowth and nutrient diffusion, preferably having pore diameter or minimum cross sectional distance ranging from about 10 $\mu$m to about 1000 $\mu$m, preferably from about 20 microns to about 200 microns; (2) a variety of pore shapes ranging from substantially circular cross-section to those with very high aspect ratios; (3) gradient in the pore size or shape across one direction of the surface texture for preferential cell culturing; (4) surface pores that become channels that run either deep into or completely through the foam for improved cell invasion, vascularization and nutrient diffusion; and (5) surface patterned foams colyophilized or coated with pharmaceutically active compounds, including, but not limited to, biological factors such as RGD'S, growth factors (PDGF, TGF-$\mu$, VEGF, BMP, FGF etc.) and the like.

A variety of absorbable polymers can be used to make micropatterned foam scaffolds according to the present invention. Examples of suitable biocompatible, bioabsorbable polymers that could be used include polymers selected from the group consisting of aliphatic polyesters, poly (amino acids), copoly(ether-esters), polyalkylenes oxalates, polyamides, tyrosine derived polycarbonates, poly (iminocarbonates), polyorthoesters, polyoxaesters, polyamidoesters, polyoxaesters containing amine groups, poly(anhydrides), polyphosphazenes, biomolecules (i.e. biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), c-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alphadiethylpropiolactone, ethylene carbonate, ethylene oxalate, 3-methyl-1,4-dioxane-2,5-dione, 3,3-diethyl 1,4-dioxan-2,5-dione, 6,8-dioxabicycloctane-7-one and polymer blends thereof. Poly (iminocarbonate) for the purpose of this invention include as described by Kemnitzer and Kohn, in the *Handbook of Biodegradable Polymers*, edited by Domb, Kost and Wisemen, Hardwood Academic Press, 1997, pages 251–272. Copoly(etheresters), for the purpose of this invention, include those copolyester-ethers described in the Journal of Biomaterials Research, Vol. 22, pages 993–1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399 (the contents of which are incorporated by reference herein in their entirety). Polyphosphazenes, co-, ter- and higher order mixed monomer based polymers made from L-lactide, D,L-lactide, lactic acid, glycolide, glycolic acid, paradioxanone, trimethylene carbonate and ϵ-caprolactone such as are described by Allcock in *The Encyclopedia of Polymer Science*, Vol. 13, pages 31–41, Wiley Intersciences, John Wiley & Sons, 1988 and by Vandorpe, Schacht, Dejardin and Lemmouchi in the *Handbook of Biodegradable Polymers*, edited by Domb, Kost and Wisemen, Hardwood Academic Press, 1997, pages 161–182. Polyanhydrides from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 (the contents of which are incorporated herein by reference in their entirety). Polyorthoesters such as those described by Heller in *Handbook of Biodegradable Polymers*, edited by Domb, Kost and Wisemen, Hardwood Academic Press, 1997, pages 99–118 (hereby incorporated herein by reference).

Currently, aliphatic polyesters are the preferred absorbable polymers for making foam scaffolds according to the present invention. Aliphatic polyesters can be homopolymers, copolymers (random, block, segmented, tappered blocks, graft, triblock,etc.) having a linear, branched or star structure. Preferred are linear copolymers. Suitable monomers for making aliphatic homopolymers and copolymers may be selected from the group consisting of, but are not limited, to lactic acid, lactide (including L-, D-, meso and D,L mixtures), glycolic acid, glycolide, ϵ-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

Elastomeric copolymers also are particularly useful in the present invention. Suitable bioabsorbable biocompatible elastomers include but are not limited to those selected from the group consisting of elastomeric copolymers of ϵ-caprolactone and glycolide (preferably having a mole ratio of ϵ-caprolactone to glycolide of from about 35:65 to about 65:35, more preferably from 45:55 to 35:65) elastomeric copolymers of ϵ-caprolactone and lactide, including L-lactide, D-lactide blends thereof or lactic acid copolymers (preferably having a mole ratio of ϵ-caprolactone to lactide of from about 35:65 to about 65:35 and more preferably from 45:55 to 30:70 or from about 95:5 to about 85:15) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of ϵ-caprolactone and p-dioxanone (preferably having a mole ratio of ϵ-caprolactone to p-dioxanone of from about from 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. Examples of suitable bioabsorbable elastomers are described in U.S. Pat. Nos. 4,045,418; 4,057,537 and 5,468,253, the contents all of which are hereby incorporated by reference in their entirety. These elastomeric polymers will have an inherent viscosity of from about 1.2 dL/g to about 4 dL/g, preferably an inherent viscosity of from about 1.2 dL/g to about 2 dL/g and most preferably an inherent viscosity of from about 1.4 dL/g to about 2 dL/g as determined at 25° C. in a 0.1 gram per deciliter (g/dL) solution of polymer in hexafluoroisopropanol (HFIP).

Preferably, the elastomers will exhibit a high percent elongation and a low modulus, while possessing good tensile strength and good recovery characteristics. In the preferred embodiments of this invention, the elastomer from which the foams are formed will exhibit a percent elongation greater than about 200 percent and preferably greater than about 500 percent. Their properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch.

The polymer or copolymer suitable for forming foam scaffolds according to the present invention for use in tissue regeneration depends on several factors. The chemical composition, spatial distribution of the constituents, the molecular weight of the polymer and the degree of crystallinity all dictate to some extent the in-vitro and in-vivo behavior of the polymer. However, the selection of the polymers to make gradient foams for tissue regeneration largely depends on (but not limited to) the following factors: (a) bioabsorption (or biodegradation) kinetics; (b) in-vivo mechanical performance; and (c) cell response to the material in terms of cell attachment, proliferation, migration and differentiation and (d) biocompatibility.

The ability of the material substrate to resorb in a timely fashion in the body environment is critical. But the differences in the absorption time under in-vivo conditions can also be the basis for combining two different copolymers. For example a copolymer of 35:65 ϵ-caprolactone and glycolide (a relatively fast absorbing polymer) is blended with 40:60 ϵ-caprolactone and (L)lactide copolymer (a relatively slow absorbing polymer) to form a foam. Such a foam could have several different physical structures depending upon the processing technique used. The two constituents can be either randomly inter-connected bicontinuous phases, or the constituents can have a gradient through the thickness or a laminate type composite with a well integrated interface between the two constituent layers. The microstructure of these foams can be optimized to regenerate or repair the desired anatomical features of the tissue that is being engineered.

One preferred embodiment of the present invention is to use polymer blends to form structures which transition from one composition to another composition in a gradient like architecture. Foams having this gradient architecture are particularly advantageous in tissue engineering applications to repair or regenerate the structure of naturally occurring tissue such as cartilage (articular, meniscal, septal, tracheal etc.), esophaguses, skin, bone and vascular tissue. For example, by blending an elastomer of ε-caprolactone-co-glycolide with ε-caprolactone-co-lactide (i.e. with a mole ratio of about 5:95) a foam may be formed that transitions from a softer spongy foam to a stiffer more rigid foam similar to the transition from cartilage to bone. Clearly other polymer blends may be used for similar gradient effects or to provide different gradients such as different absorption profiles, stress response profiles, or different degrees of elasticity. Additionally, these foams can be used for organ repair replacement or regeneration strategies that may benefit from these unique scaffolds, including but are not limited to, spine disc, cranial tissue, dura, nerve tissue, liver, pancreas, kidney, bladder, spleen, cardiac muscle, skeletal muscle, tendons, ligaments and breast tissues.

These elastomeric polymers may be foamed by lyophilization, supercritical solvent foaming (i.e., as described in EP 464,163 B1), gas injection extrusion, gas injection molding or casting with an extractable material (i.e., salts, sugar or any other means known to those skilled in the art).

The micropatterned foam scaffolds of the present invention may be made by a polymer-solvent phase separation technique. Generally, a polymer solution can be separated into two phases by any one of the four techniques: (a) thermally induced gelation/crystallization; (b) non-solvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous structure of density less than the bulk polymer and pores in the micrometer ranges see Microcellular Foams Via Phase Separation, J. Vac. Sci. Technolol., A. T. Young, Vol. 4(3), May/Jun 1986. The steps involved in the preparation of these foams include choosing the right solvents for the polymers to be lyophilized and preparing a homogeneous solution. Next, the polymer solution is subjected to a freezing and vacuum drying cycle. The freezing step phase separates the polymer solution and vacuum drying step removes the solvent by sublimation and/or drying leaving a porous polymer structure or an interconnected open cell porous foam.

Suitable solvents for preferred absorbable aliphatic polyesters include, but are not limited to, solvents selected from a group consisting of formic acid, ethyl formate, acetic acid, hexafluoroisopropanol (HFIP), cyclic ethers (i.e. THF, DMF, and PDO), acetone, acetates of C2 to C5 alcohol (such as ethyl acetate and t-butylacetate),glyme (i.e. monoglyme, ethyl glyme, diglyme, ethyl diglyme, triglyme, butyl diglyme and tetraglyme) methylethyl ketone, dipropyleneglycol methyl ether, lactones (such as γ-valerolactone, δ-valerolactone, β-butyrolactone, γ-butyrolactone) 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, the preferred solvent is 1,4-dioxane. A homogeneous solution of the polymer in the solvent is prepared using standard techniques.

The applicable polymer concentration or amount of solvent that may be utilized will vary with each system. As a general guideline, the amount of polymer in the solution can vary from about 0.5% to about 90% and, preferably, will vary from about 0.5% to about 30% by weight, depending to a large extent on the solubility of the polymer in a given solvent and the final properties of the foam desired.

Additionally, solids may be added to the polymer-solvent system. One of the purposes of the added particles could be to modify the composition of the resulting foam surfaces. As the particles settle out of solution to the bottom surface, regions will be created that will have the composition of the added solids, not the foamed polymeric material. In another embodiment, the added solids may be more concentrated near the top, sides, or bottom of the micropatterned foam causing compositional changes on all these surfaces. An example would be if the added solids were metallic and the mold were made of a magnetic material, or vice versa. The solids added to the polymer-solvent system preferably will not react with the polymer or the solvent. Solids such as barium sulfate particles may also be added as markers to make the constructs radio opaque. Suitable solids include materials that promote tissue regeneration or regrowth, buffers, reinforcing materials or porosity modifiers. Suitable solids include, but are not limited to, particles of demineralized bone, calcium phosphate particles, Bioglass particles or calcium carbonate particles for bone repair, leachable solids for pore creation and particles of bioabsorbable polymers not soluble in the solvent system as reinforcing or to create pores as they are absorbed. Suitable leachable solids include but are not limited nontoxic leachable materials selected from the group consisting of salts (i.e. sodium chloride, potassium chloride, calcium chloride, sodium tartrate, sodium citrate, and the like) biocompatible mono and disaccharides (i.e. glucose, fructose, dextrose, maltose, lactose and sucrose), polysaccharides (i.e. starch, alginate, chitosan), water soluble proteins (i.e. gelatin and agarose). In addition, non-bioabsorbable materials may be added, such as biocompatible metals, including but not limited to stainless steel, coblat chrome, titanium and titanium alooys, or bioinert ceramic particles, including but not limited to alumina, zirconia, and calcium sulfate particles, or particles of non-bioabsorbable polymers including but not limited to polyethylene, PVA, PMMA, silicone, PEO, PEG, and polyurethanes, or natural biopolymers, including but not limited to cellulose (wood) particles, chitin, keratin, silk, or collagen particles. Generally all of these materials will have an average diameter of less than about 1.0 mm and preferably will have an average diameter of about 50 to about 500 microns. The particles will generally constitute from about 1 to about 50 volume percent of the total volume of the particle and polymer-solvent mixture (wherein the total volume percent equals 100 volume percent). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. This process is described in U.S. Pat. No. 5,514,378, hereby incorporated herein by reference (see column 6). Preferably the foam will be dried after the leaching process is complete at low temperature and/or vacuum to minimize hydrolysis of the foam unless accelerated absorption of the foam is desired.

After the polymer solvent mixture is formed the mixture is then solidified. For a specific polymer-solvent system, the solidification point, the melt temperature and the apparent glass transition of the polymer-solvent system can be determined using standard differential scanning calorimetric (DSC) techniques. In theory, but in no way limiting the scope of the present invention, it is believed that as a polymer solvent system is cooled down an initial solidification occurs at about or below the freezing point of the solvent. This corresponds to the freezing of a substantial portion of the solvent in the system. The initial freezing appears as a first exothermic peak. A second freezing point occurs when the remaining solvent associated with the polymer solidifies. The second freezing point is marked by a second exothermic peak. The apparent Tg is the temperature at which the fully frozen system displays the first endothermic shift on reheating.

An important parameter to control is the rate of freezing of the polymer-solvent system. The type of pore morphology that gets locked in during the freezing step is a function of the solution thermodynamics, freezing rate, temperature to which it is cooled, concentration of the solution, homogeneous or heterogenous nucleation etc. Detailed description of these phase separation phenomenon can be found in the references provided herein (See Microcellular Foams Via Phase Separation, A. T. Young, J. Vac. Sci. Technol., Vol. A 43, May/Jun 1986; and Thermodynamics of Formation of Porous Poymeric Membrane from Solutions, S. Matsuda, Polymer J., Vol. 23, No. 5, pp 435–444, 1991.

Foam scaffolds of the present invention are made by injecting, pouring, or otherwise placing, the polymer solution in contact with a micropatterned mold and cooling the mold in an appropriate bath or on a refrigerated shelf such that the foam is lyophilized, thereby providing a micropatterned, lyophilized foam. By micropatterned, it is meant that the mold comprises on at least one surface thereof that is to be placed in contact with the polymer solution a three-dimensional negative configuration of a predetermined and designed micropattern to be disposed on and integral with at least one surface of the foam scaffold. The predetermined design will vary depending on the actual contemplated use of the foam.

FIG. 1 shows a perspective view of mold 10 comprising base 20, side walls 30, and top surface 40 of base 20. Patterning strips 52, 54, 56, and 58 are disposed parallel on top surface 40. Although parallel alignment of four patterning strips 52, 54, 56, and 58 is shown in FIG. 1, any number of strips, as well as any desired alignment, may be envisioned.

Figure 2:
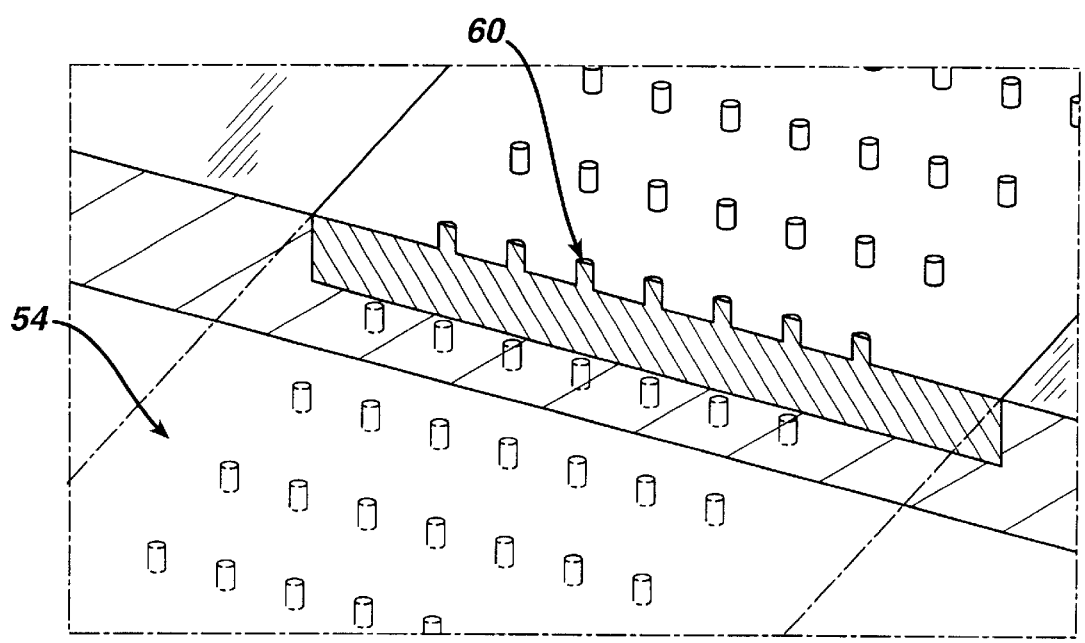
FIG. 2 is a magnified view of the textured insert for the mold pictured in FIG. 1.
Figure 3:
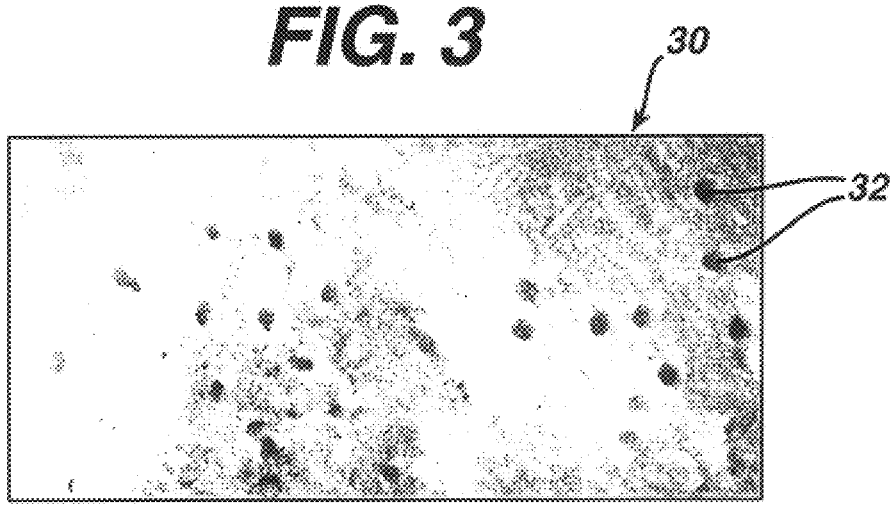
FIG. 3 is a top planar view of a foam scaffold having a random array of columnar pores of varying size.

FIG. 2 is an enlarged view of a section of mold 10. Patterning strip 54 is seen on top surface 40 of base 20. Patterning pins 60 protrude from the surface of patterning strip 54, thus providing a three-dimensional negative configuration of the predetermined and designed micropattern to be disposed on and integral with a surface of the foam. Though patterning pins 60 on FIG. 2 are shown with a circular cross section and are arranged in an ordered array, actual predetermined and desired patterning pin cross sections and array alignments will depend on the particular use and performance required of the resulting micropatterned foam scaffold. In FIG. 3, foam 30 comprises an irregularly space columnar pores 32 of varying diameter or minimum cross-sectional distance.

Figure 4:
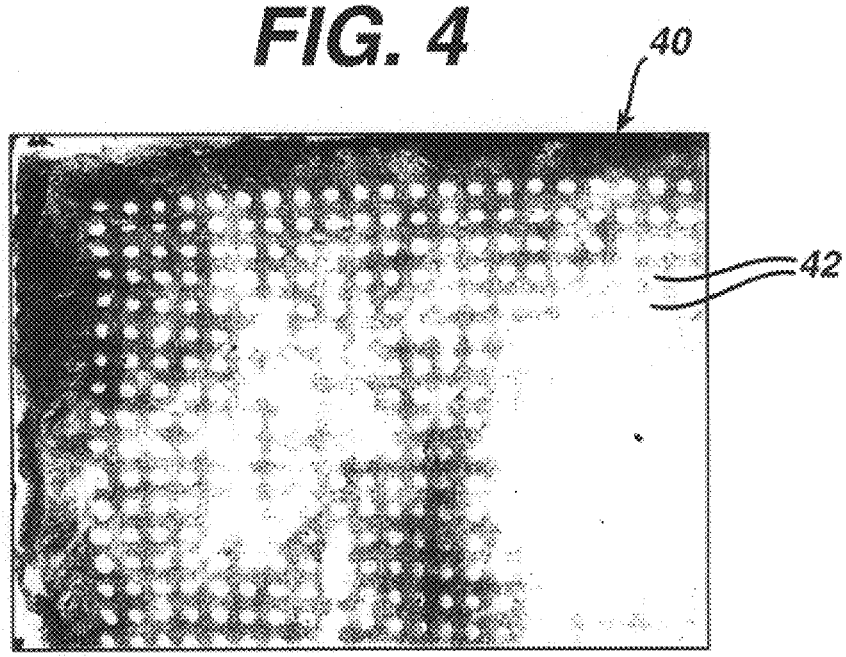
FIG. 4 is a top planar view of a foam scaffold according to the present invention having an array of regularly spaced columnar pores.
Figure 7:
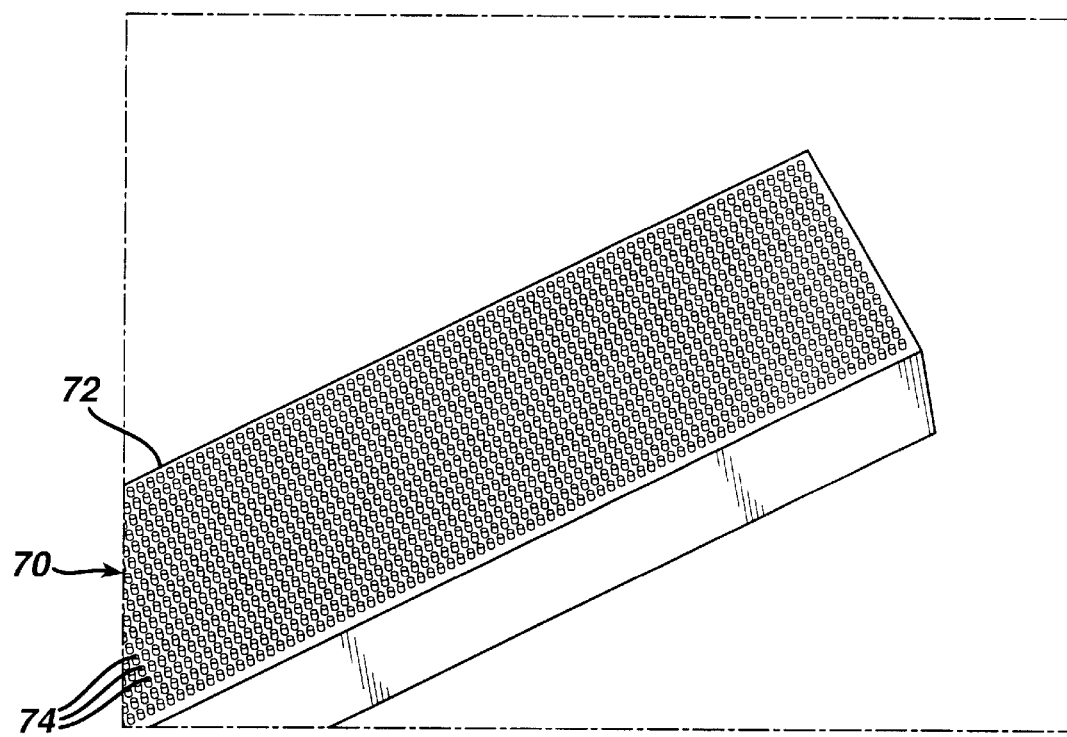
FIG. 7 is a top elevation of the mold used to prepare the foam of FIG. 4.
Figure 8:
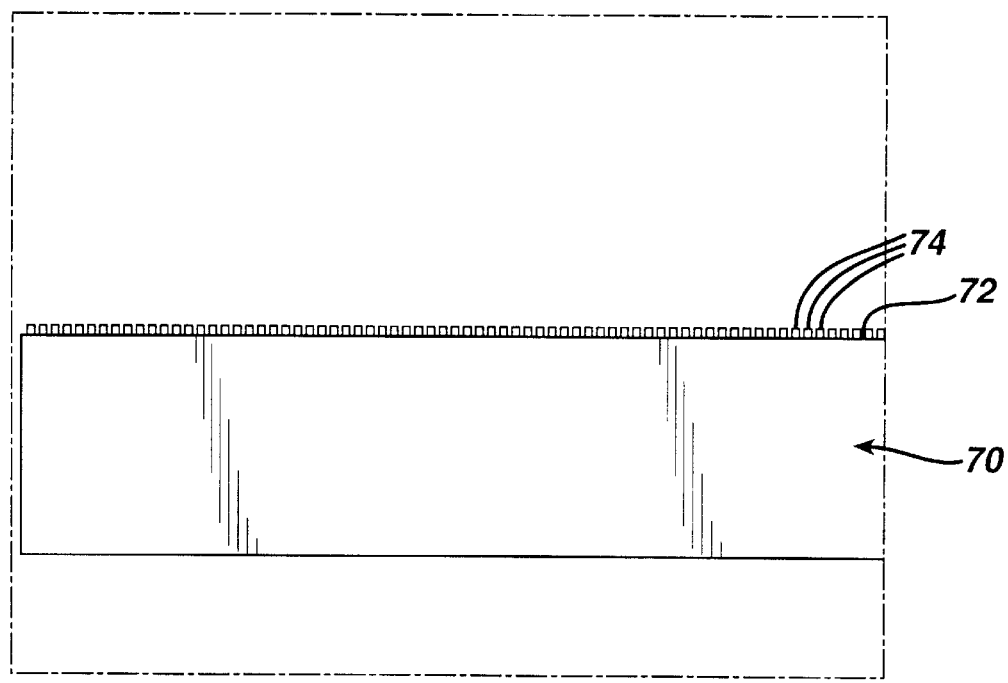
FIG. 8 is a side view of the mold used to prepare the foam of FIG. 4.

In FIG. 4, foam 40 comprises an array of regularly spaced columnar pores 42. In FIG. 7, mold 70, used to make foam 40 in FIG. 4, surface 72 comprises an array of regularly spaced projections 74, which collectively form a three-dimensional negative configuration of the micropattern of foam 40 in FIG. 4. FIG. 8 shows a side view of mold 70 with projections 74.

Any material that is easy to process to the resolution needed and that will not dissolve in the solvent can be used to make a micropatterned mold for this process. This includes not only metals, but also ceramics and some polymers. Metals suitable for the mold include without limitation aluminum, stainless steel and other metal alloys. Ceramic materials include without limitation alumina, zirconia, and silica. The preferred metal is aluminum, while alumina and silicone are the preferred ceramic and polymer, respectively. These materials were chosen for their low cost, resistance to corrosion in solvents, and ease of processability.

Molds of this type can be made by a variety of micromolding or micromachining techniques that are known, including injection molding, laser drilling, laser cutting, sputter processing using ion or electron beam milling, YAG laser cutting and electric discharge machining, otherwise known as the "EDM" process. The preferred method is to use electro-discharge machining, a common micromachining technique, in which a small electrode discharges on the substrate, thus etching the substrate with the shape of the electrode as it discharges. This method is cost effective, accurate and reproducible. The method lends itself to a wide variety of materials and geometries.

Alternatively, the polymer solution can be atomized by an atomizer and sprayed onto a cold-patterned surface, i.e. a mold, causing solidification of the spray layer by layer. The cold surface can be a medical device or part thereof or a film. The shape of the solidified spray will be similar to the shape of the surface it is sprayed onto. Alternatively, the mixture after solidification can be cut or formed to shape while frozen. Using these and other processes the foams can be made or molded in a variety of shapes and sizes (i.e. tubular shapes, branched tubular shapes, spherical shapes, hemispherical shapes, three-dimensional polygonal shapes, ellipsoidal shapes (i.e. kidney shaped), toroidal shapes, conical shapes, frusta conical shapes, pyramidal shapes, both as solid and hollow constructs and combination thereof).

Alternatively, another method to make shaped foamed parts with micropatterned surfaces is to use a cold finger (a micropatterned metal part whose surface represents the inside of the foam to fabricate). The cold finger is dipped into a solution of polymer in an appropriate solvent and removed. This is much like dipping an ice cream pop into warm chocolate that freezes to a hard, cold skin, or dipping a form into a latex of rubber to form gloves or condoms. The thickness and morphology of the foam produced are a function of the temperature, dwell time and withdrawal rate of the cold finger in the mixture. Longer dwell, colder finger and slower withdrawal will produce a thicker coating. After withdrawal, the cold finger is placed on a fixture of large thermal mass that is in contact with the refrigerated tray of the lyophilizer. From this point the primary and secondary drying processes are as described above. This method is particularly well suited to making tubes, branched tubular structures or sleeves that may be shaped to fit devices or portions of an animal's anatomy (for repair, regeneration or augmentation of tissue).

Additionally, the polymer solution can be solidified with various inserts incorporated with the solution such as films, scrims, woven, nonwoven, knitted or braided textile structures. Additionally, the solution can be prepared in association with another structure such an orthopedic implant (e.g. screws, pins, nails, and plates) or vascular or branched tubular construct (as a scaffold for a vascularized or ducted organ). These inserts will be made of at least one biocompatible material and may be non-absorbable, absorbable or a combination thereof.

The polymer solution in a micropatterned mold undergoes directional cooling through the wall of the mold that is in contact with the freeze dryer shelf, which is subjected to a thermal cycle. The mold and its surface can be made from virtually any material that does not interfere with the polymer-solvent system, though it is preferred to have a highly conducting material. The heat transfer front moves upwards from the lyophilizer shelf through the mold wall into the polymer solution. The instant the temperature of the mixture goes below the gelation and/or freezing point the mixture also phase separates.

The morphology of this phase-separated system is locked in place during the freezing step of the lyophilization process and the creation of the open pores is initiated by the onset of vacuum drying resulting in the sublimation of the solvent. However, the mixture in container or mold that is cooled from a heat sink will solidify prior to completely freezing. Although the mixture may appear solid, initially there appears to be some residual solvent associated with the polymer that has not crystallized. It is theorized, but in no way limiting the present invention, that a freezing front moves through the mixture from the heat sink to complete the solidification after the mixture has apparently solidified. The material in front of the freezing front at a given time will not be as cold as the material behind the front and will not be in a completely frozen state.

The process cycle for producing biocompatible foams is significantly reduced by performing the sublimation step above the apparent glass transition temperature and below the solidification temperature of the mixture (preferably just below the solidification temperature). The combined cycle time of (freezing+primary drying+secondary drying) is much faster than is described in the prior art. For example, the combined cycle for aliphatic polyesters using volatile solvents is generally less than 72 hours, preferably less than 48 hours, more preferably less than 24 hours and most preferably less than 10 hours. In fact the combined cycle can be performed with some aliphatic polyesters in less than 3 hrs for foams of thickness 1 mm or less; less than 6 hrs for foams of thickness around 2 mm and less than 9 hrs for foams of thickness around 3 mm. Compare this with prior art which is typically 72 hours or greater. The residual solvent concentrations in these foams made by this process will be very low. As described for aliphatic polyesters foams made using 1,4-dioxane as a solvent the residual concentration of 1,4-dioxane was less than 10 ppm (parts per million) more preferably less than 1 ppm and most preferably less than 100 ppb (parts per billion).

Various proteins (including short chain peptides), growth agents, chemotatic agents and therapeutic agents (antibiotics, analgesics, anti-inflammatories, antirejection (e.g. immunosuppressants) and anticancer drugs), or ceramic particles can be added to the foams during processing, adsorbed onto the surface or back filled into the foams after the foams are made. For example, the pores of the foam may be partially or completely filled with biocompatible resorbable synthetic polymers or biopolymers (such as collagen or elastin) or biocompatible ceramic materials (such as hydroxyapatite) and combinations thereof (that may or may not contain materials that promote tissue growth through the device). Suitable materials include but are not limited to autograft, allograft, or xenograft bone, bone marrow, morphogenic proteins (BMP's), epidermal growth factor (EGF), fibroblast growth factor (FGF), platelet derived growth factor (PDGF), insulin derived growth factor (IGF-I and IGF-II), transforming growth factors (TGF-β), vascular endothelial growth factor (VEGF) or other osteoinductive or osteoconductive materials known in the art. Biopolymers could also be used as conductive or chemotactic materials, or as delivery vehicles for growth factors. Examples could be recombinant or animal derived collagen or elastin or hyaluronic acid. Bioactive coatings or surface treatments could also be attached to the surface of the materials. For example, bioactive peptide sequences (RGD's) could be attached to facilitate protein adsorption and subsequent cell tissue attachment. Therapeutic agents may also be delivered with these foams.

In another embodiment of the present invention, the polymers and blends that are used to form the foam can contain therapeutic agents. To form these foams, the previously described polymer would be mixed with a therapeutic agent prior to forming the foam or loaded into the foam after it is formed. The variety of different therapeutic agents that can be used in conjunction with the foams of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1–7), bone morphogenic-like proteins (i.e. GFD-5, GFD-7 and GFD-8), epidermal growth factor (EGF), fibroblast growth factor (i.e. FGF 1–9), platelet derived growth factor (PDGF), insulin like growth factor (IGF-I and IGF-II), transforming growth factors (i.e. TGF-βI-III), vascular endothelial growth factor (VEGF)); and other naturally derived or genetically engineered proteins, polysaccharides, glycoproteins, or lipoproteins. These growth factors are described in *The Cellular and Molecular Basis of Bone Formation and Repair* by Vicki Rosen and R. Scott Thies, published by R. G. Landes Company hereby incorporated herein by reference.

Micropatterned foams containing bioactive materials may be formulated by mixing one or more therapeutic agents with the polymer used to make the foam or with the solvent or with the polymer-solvent mixture and foamed. Alternatively, a therapeutic agent could be coated on to the foam preferably with a pharmaceutically acceptable carrier. Any pharmaceutical carrier can be used that does not dissolve the foam. The therapeutic agents, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids the drug will be released. The micropatterned surface, specifically the area of the surface pores as well as the percent porosity of the surface, will determine the surface area of the foam and can be changed to alter the rate of drug release. If the drug is incorporated into the foam, then as the foam undergoes gradual degradation (mainly through hydrolysis) the drug will be released. The release rate of the drug will depend in part on the solubility of the drug in water. The preferable micropatterned foam delivery vehicle would have a larger pore size and a lower porosity if extended drug release is desired. On the other hand, the preferable micropatterned foam delivery vehicle would have a smaller pore size and higher porosity if rapid drug release is desired. Preferred pore area will range from less than 1 square micron to 2,000 square microns. The preferred percent porosity will range from 10 to 97 percent. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

The micropatterned foam may also serve as a scaffold for the engineering of tissue. The micropatterned surface structure would be conducive to growth of cells. As outlined in previous patents (Vacanti, U.S. Pat. No. 5,770,417), cells can be harvested from a patient (before or during surgery to repair the tissue) and the cells can be processed under sterile conditions to provide a specific cell type (i.e., pluripotent cells, stem cells or precursor cells such as the mesenchymal stem cells described in Caplan, U.S. Pat. No. 5,486,359, etc.). Suitable cell that may be contacted or seeded into the foam scaffolds include, but are not limited to, myocytes, adipocytes, fibromyoblasts, ectodermal cell, muscle cells, osteoblast (i.e. bone cells), chondrocyte (i.e. cartilage cells), endothelial cells, fibroblasts, pancreatic cells, hepatocyte, bile duct cells, bone marrow cells, neural cells, genitourinary cells (including nephritic cells) and combinations thereof. Various cellular strategies could be used with these scaffolds (i.e., autogenous, allogenic, xenogeneic cells etc.). The cells could also contain inserted DNA encoding a protein that could stimulate the attachment, proliferation or differentiation of tissue. The foam would be placed in cell culture and the cells seeded onto or into the structure. The foam would be maintained in a sterile environment and then implanted into the donor patient once the cells have invaded the microstructure of the device. The in vitro seeding of cells could provide for a more rapid development and differentiation process for the tissue. It is clear that cellular differentiation and the creation of tissue specific extracellular matrix is critical for the tissue engineering of a functional implant.

The micropatterned foam scaffolds of the present intention may be sterilized using conventional sterilization process such as radiation based sterilization (i.e. gamma-ray), chemical based sterilization (ethylene oxide) or other appropriate procedures. Preferably the sterilization process will be with ethylene oxide at a temperature between 52–55° C. for a time of 8 hours or less. After sterilization the foam scaffolds may be packaged in an appropriate sterilize moisture resistant package for shipment and use in hospitals and other health care facilities.

The following examples are illustrative of the principles and practice of this invention, although not limited thereto. Numerous additional embodiments within the scope and spirit of the invention will become apparent to those skilled in the art.

In these examples certain abbreviations are used such as PCL to indicate polymerized ε-caprolactone, PGA to indicate polymerized glycolide, PLA to indicate polymerized (L)lactide. Additionally, the percentages in front of the copolymer indicates the respective mole percentages of each constituent.

The polymers used in the following examples either were a 35/65 copolymer of PCL/PGA, a 60/40 copolymer of PLA/PCL, or a 1:1 blend of the two.

EXAMPLE 1

Preparation of a micropatterned foam with irregularly spaced columnar pores.

This example describes the making of a foam with vertical channels that would provide pathways for nutrient transport and guided tissue regeneration.

Step A. Preparing 10% wt./wt. homogeneous solution of 35/65 PCL/PGA in 1,4-Dioxane A 10% wt./wt. polymer solution was prepared by dissolving 1 part 35/65 PCL/PGA with 9 parts of solvent 1,4-dioxane (Fisher Scientific, Fair Lawn, N.J.). The solution was prepared in a flask with a magnetic stir bar. To dissolve the copolymer completely, the mixture was gently heated to 70° C. and continuously stirred for 5 hours. A clear homogeneous solution was then obtained by filtering the solution through an extra coarse porosity filter (Pyrex brand extraction thimble with fritted disc) using dry nitrogen to help in the filtration of this viscous solution.

Step B. Preparing a micropatterned silicone mold providing irregularly spaced columnar pores A silicone sheet and three different diameter metal pins of 130 microns, 200 microns, and 250 microns were prepared. Each pin was cut to a 1-inch length. The pins were inserted into the silicon sheet in an irregular array.

Step C. Lyophilization

A laboratory scale lyophilizer (Model Freezemobile 6 of VIRTIS) was used in this experiment. The freeze dryer was powered up and the shelf chamber was maintained at 20° C. at ambience for approximately 30 minutes. Thermocouples to monitor the shelf temperature were attached for monitoring. The homogeneous polymer solution prepared in Step A was poured into the aluminum mold just before the actual start of the cycle. The aluminum mold was 5 inches by 5 inches and had a smooth floor and smooth walls. The lip height of the mold was 2.5 cm. The silicone sheet prepared at Step B was laid on the mold floor.

The aluminum mold with the solution was placed on the shelf of the lyophilizer, which was maintained at 20° C. The cycle was started and the shelf temperature was held at 20° C. for 30 minutes for thermal conditioning. Then, the solution was cooled to −5° C. by cooling the shelf to −5° C. After 60 minutes of freezing at −5° C., a vacuum was applied to initiate primary drying of the dioxane by sublimation. Primary drying under vacuum at −5° C. removed most of the solvent. At the end of this drying stage the vacuum level reached was about 100 mTorr. Secondary drying under a 100 mTorr vacuum was done in two stages to remove the adsorbed dioxane. In the first stage, the shelf temperature was raised to 5° C. and held at that temperature for 1.5 hour. At the end of the first stage the second stage of drying was begun. In the second stage of drying, the shelf temperature was raised to 20° C. and held at that temperature for 1.5 hours. At the end of the second stage, the lyophilizer was brought to room temperature and the vacuum was broken.

The resulting foam depicted in FIG. 3 was about 2 mm thick. The conditions described herein are typical and operating ranges depend on factors such as concentration of the solution, polymer molecular weights and compositions, volume of the solution, mold parameters, machine variables like cooling rate, and heating rates.

EXAMPLE 2

Preparation of a foam with regularly spaced columnar pores.

This example describes the making of a 40/60 PCL/PLA foam with vertical channels that would provide pathways for nutrient transport and guided tissue regeneration.

Step A. Preparing 5% wt./wt. homogeneous solution of 40/60 PCL/PLA in 1,4-Dioxane A 5% wt./wt. polymer solution is prepared by dissolving 1 part of Polymer of 40/60 PCL/PLA with 19 parts of the solvent -1,4-dioxane. This solution is prepared as described in Example 1.

Step B. Preparing a metal mold providing regularly spaced columnar pores

An aluminum mold with an array of regularly spaced pins was designed and created via electro discharge machining. Pins were 500 microns in height and 100 microns in diameter. The spacing between pins was 400 microns.

Step C. Lyophilization

This foam was processed as described in Example 1, Step C, using the mold and insert prepared in above Step B. The resulting foam is depicted in FIG. 4. These columnar pores optimally will have a diameter ranging from about 10 microns to about 1,000 microns, with an optimal spacing of from about 10 microns to about 1,000 microns, depending on the specific application. These pores can act as channels, not only allowing tissue ingrowth and vascularization of the area, but also allowing diffusion of nutrients and waste products through the newly formed tissue.

EXAMPLE 3

Preparation of a foam with various shaped columnar pores.

Step A. Preparing 5% wt./wt. homogeneous solution of 50:50 by weight of (35/65 PCL/PGA):(40/60 PCL/PLA) in 1,4-Dioxane A 5% wt./wt. polymer solution of 50:50 by weight of (35/65 PCL/PGA):(40/60 PCL/PLA) is prepared by dissolving 1 part of Polymer (0.5 part of 35/65 PCL/PGA and 0.5 part of 40/60 PCL/PLA) with 19 parts of the solvent 1,4-dioxane. This solution is prepared as described in Example 1, Step A.

Step B. Preparing a silicone mold with pins having various cross-sectional shapes The silicone sheet containing arrays of pins with various cross-sectional shapes, such as squares, hexagons, rectangles, circles, ovals, etc. was prepared as in Example 1, Step B. These irregularly shaped columnar pores will optimally have minimal cross-sectional distances ranging from about 10 microns to about 1,000 microns, preferably from about 20 to about 200 microns, with an optimal spacing of about 10 microns to about 1,000 microns, depending on the specific application. The sheet is disposed on the mold floor prior to being placed in contact with the polymer solution.

Step C. Lyophilization

Figure 5:
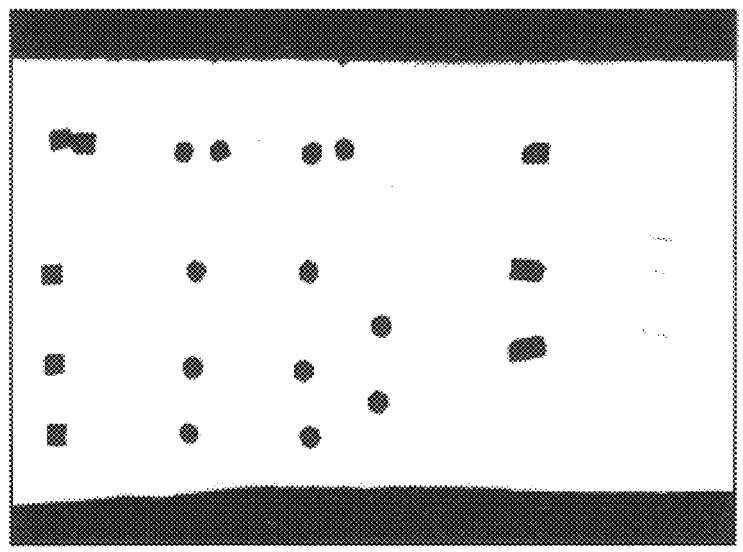
FIG. 5 is a micrograph of a top planar view of a foam scaffold having columnar pores with different cross-sectional shapes.

This foam is processed as described in Example 1, Step C using the mold prepared in the Step B, above. FIG. 5 depicts a surface of the foam produced following the process set forth in this example.

EXAMPLE 4

Preparation of a micropatterned foam with pyramidal frustum shaped pores.

Step A. Preparing 5% wt./wt. homogeneous solution of 40/60 PCL/PGA in 1,4-Dioxane A 5% wt./wt. polymer solution is prepared by dissolving 1 part of Polymer of 40/60 PCL/PLA with 19 parts of the solvent 1,4-dioxane. This solution is prepared as described in Example 1, Step A.

Step B. Preparing a ceramic mold providing pyramidal frustum shaped pores

An alumina (A1203) mold with pyramidal frustum shaped protrusions having regular spacing was injection molded. The lengths of the lower and upper bases are 1,300 microns and 400 microns, respectively. The height of the frustum of each pyramid and the spacing between two lower bases are 1,000 microns and 700 microns, respectively.

Step C. Lyophilization

Figure 6:
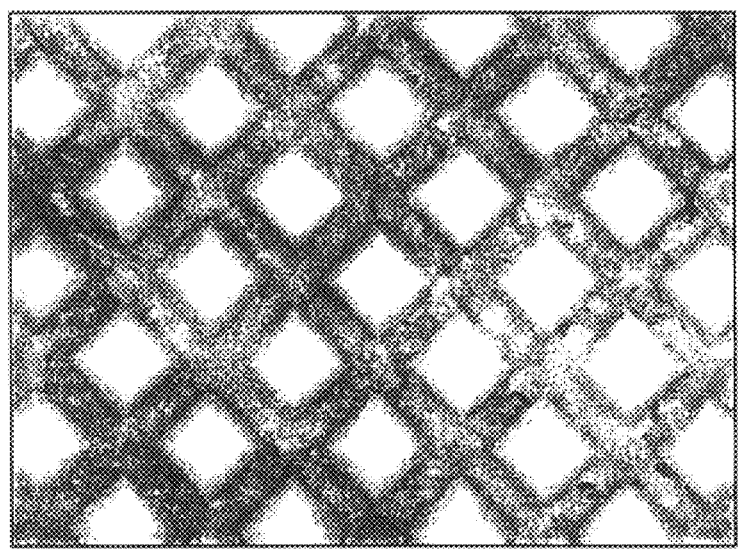
FIG. 6 is a micrograph of a top planar view of a foam surface made from a mold having a regular pattern of protrusions in the shape of pyramidal frusta.

This foam was processed as described in Example 1 using the mold prepared in Step B, above. FIG. 6 shows a foam produced following the process set forth in this example.

We claim:

1. A method of making a foam, the method comprising:
   contacting a polymer solution with a surface of a mold, said solution comprising dissolved therein a biocompatible polymer, said mold comprising disposed on said surface a three-dimensional negative configuration of a predetermined micropattern to be disposed on and integral with at least one surface of said foam,
   lyophilizing said solution while in contact with said surface of said mold, thereby providing a lyophilized, micropatterned foam; and
   removing said lyophilized, micropatterned foam from said mold.

2. The method of claim 1 wherein said micropattern is effective to facilitate repair, ingrowth or regeneration of tissue.

3. The method of claim 1 wherein said micropattern is effective to facilitate delivery of a therapeutic agent.

4. The method of claim 1 wherein said micropattern is effective to facilitate delivery of a protein.

5. The method of claim 1 wherein said polymer is bioabsorbable.

6. The method of claim 5 wherein the bioabsorbable polymer is selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups poly(anhydrides), polyphosphazenes, tyrosine derived polycarbonates, and biopolymers.

7. The method of claim 6 wherein the bioabsorable polymer is an aliphatic polyester.

8. The method of claim 7 wherein the aliphatic polyester is selected from the group consisting of homopolymers and copolymers of lactide, lactic acid, glycolide, glycolic acid, $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one, 1,5,8,12-tetraoxacyclotetradecane-7,14-dione, 1,5-dioxepan-2-one, and 6,6-dimethyl-1,4-dioxan-2-one.

9. The method of claim 7 wherein the aliphatic polyester is an elastomer.

10. The method of claim 9 wherein the elastomer is selected from the group consisting of copolymers of ε-caprolactone and glycolide; copolymers of ε-caprolactone and (L)lactide, copolymers of p-dioxanone (1,4-dioxan-2-one) and (L)lactide, copolymers of ε-caprolactone and p-dioxanone, copolymers of p-dioxanone and trimethylene carbonate, copolymers of trimethylene carbonate and glycolide, copolymer of trimethylene carbonate and (L)lactide.

11. The method of claim 1 wherein said micro-patterned, lyophilized foam comprises a therapeutic agent.

12. The method of claim 11 wherein said therapeutic agent is selected from the group consisting of antiinfectives, hormones, analgesics, anti-inflammatory agents, growth factors, chemotherapeutic agents, anti-rejection agents prostaglandins, and RDG peptides.

13. The method of claim 1 wherein said micropatterned, lyophilized foam comprises a protein.

14. The method of claim 1 wherein said micropatterened, lyophilized foam comprises solid particles to modify a surface of said foam.

15. The method of claim 1 wherein said micropattern comprises irregularly spaced or regularly spaced columnar pores.

16. The method of claim 15 wherein the diameter or minimum cross-sectional distance of said pores is from about 10 microns to about 1,000 microns and wherein the spacing between said pores is from about 10 microns to about 1,000 microns.

17. The method of claim 1 wherein said micropattern comprises irregularly shaped columnar pores.

18. The method of 17 wherein the minimum cross-sectional distance of said pores is from about 10 microns to about 1,000 microns and wherein the spacing between said pores ranges from about 10 microns to about 1,000 microns.

19. The method of claim 18 wherein said minimum cross-sectional distance is from about 20 microns to about 200 microns.

* * * * *